(12) United States Patent
Saiger

(10) Patent No.: US 6,514,999 B1
(45) Date of Patent: Feb. 4, 2003

(54) USE OF AN AGENT FOR TREATING THE SYMPTOMS OF PARKINSON'S DISEASE

(76) Inventor: Lothar Saiger, Hauptstrasse 3, D-88525 Dürmentingen (DE)

( * ) Notice: Subject to any disclaimer, the term of this patent is extended or adjusted under 35 U.S.C. 154(b) by 0 days.

(21) Appl. No.: 09/857,313

(22) PCT Filed: Dec. 9, 1998

(86) PCT No.: PCT/DE98/03612

§ 371 (c)(1),
(2), (4) Date: Aug. 8, 2001

(87) PCT Pub. No.: WO00/32232

PCT Pub. Date: Jun. 8, 2000

(30) Foreign Application Priority Data

Dec. 3, 1998 (DE) ......................... 198 55 704

(51) Int. Cl.[7] .............................. A61K 31/44
(52) U.S. Cl. ...................... 514/354; 514/626
(58) Field of Search ................. 514/354, 626

(56) References Cited

U.S. PATENT DOCUMENTS

| 5,190,763 | A | | 3/1993 | Ayer et al. | |
|---|---|---|---|---|---|
| 5,484,608 | A | | 1/1996 | Rudnic et al. | |
| 5,668,117 | A | | 9/1997 | Shapiro | |
| 6,133,299 | A | * | 10/2000 | Taylor, Jr. et al. | .......... 514/353 |

FOREIGN PATENT DOCUMENTS

| EP | 0 878 191 | 11/1998 |
|---|---|---|
| WO | WO98/00142 | 1/1998 |

OTHER PUBLICATIONS

Mura et al. (1998) "Reevaluation of the Striatal Role in the Expression of Turning Behavior in the Rat Model of Parkinson's Disease", *Brain Research*, vol. 808(1) pp. 48–55.
Bathien et al. (1977) "Reciprocal Continuous Inhibition in Rigidity of Parinsonism", *Journal of Neurology, Neurosurgery and Psychiatry*, vol. 40(1) pp. 20–4.
Furuya et al. (1998) "Successful Perioperative Management of a Patient with Parkinson's Disease by Enteral Levodopa Administration Under Propofol Anesthesia" *Anesthesiology* vol. 89(1) pp. 261–263.
Salata et al. (1982) "Amantadine–induced Diastolic Depolarization and Automatically in Ventricular Muscle", *Circulation Research* vol. 51(6) pp. 722–732.
Dostrovsky et al. (1993) "Microinjection of Lidocaine into Human Thalamus: A Useful Tool in Stereotactic Surgery", *Stereotactic and Functional Neurosurgery* vol. 60(4) pp. 168–174.

* cited by examiner

Primary Examiner—Dwayne C. Jones
Assistant Examiner—C. Delacroix-Muirheid
(74) Attorney, Agent, or Firm—Collard & Roe P.C.

(57) ABSTRACT

With an agent for preparing a medication for treating the symptoms of Parkinson's disease, one obtains more effective treatment of the symptoms of said disease compared to classical treatment by a combination of effective substances comprising a substance increasing dopamine concentration in the synaptic cleft of the neurons of the brain along with a local anesthetic of the anilide group.

21 Claims, No Drawings

USE OF AN AGENT FOR TREATING THE SYMPTOMS OF PARKINSON'S DISEASE

CROSS REFERENCE TO RELATED APPLICATIONS

Applicant claims priority under 35 U.S.C. § 119 of German Application No. 198 55 704.3 filed Dec. 3, 1998. Applicant claim priority under 35 U.S.C. § 120 of PCT/DE98/03612 filed Dec. 9, 1998. The international application under PCT article 21(2) was not published in English.

This invention relates to a use of an agent having a substance increasing the dopamine concentration in the synaptic cleft of the neurons of the brain.

The invention relates to an agent for preparing a medication for treating the symptoms of Parkinson's disease.

In the classical treatment of Parkinson's disease the main effective substance used is levodopa, also known as L-Dopa. Levodopa is a precursor of dopamine and, unlike the latter, capable of crossing the blood-brain barrier after an application. After crossing the blood-brain barrier, levodopa is converted to dopamine in the brain. The substance dopamine acts in the brain as a neurotransmitter in the synaptic cleft of the neurons of the brain in such a way as to promote signal transmission from one cell to another. The concentration of dopamine is deficient in the brains of persons suffering from Parkinson's disease so that signal transmission is impaired from one neuron to another in the brain. The administration of levodopa to parkinsonian patients increases dopamine concentration in the synaptic cleft of the neurons of the brain, thereby improving signal transmission between the neurons of the brain and improving control of motor and intellectual processes.

In addition to levodopa, the classical treatment of Parkinson's disease involves the administration of substances which promote the effect of dopamine called dopamine-promoting agonists. Dopamine-promoting agonists generally act in such a way that dopamine concentration in the synaptic cleft of the neurons of the brain remains increased through inhibition of the breakdown of dopamine there. Normal breakdown of dopamine is caused by it being broken down to noradrenaline by an enzyme, monooxygenase.

Formation of monooxygenase can be inhibited by certain dopamine-promoting agonists so that dopamine can only be broken down to noradrenaline to a diminished degree and a given concentration of dopamine in the synaptic cleft is consequently maintained longer. Alternatively the mode of action of dopamine-promoting agonists can be based on releasing dopamine stored in storage sites of the brain and inhibiting reassimilation in the storage site. Dopamine-promoting agonists include bromocriptine, selegiline, amantadine, pergolide mesylate or tolcapone. A further known dopamine-promoting agonist is NORMA BRAIN® (piracetam) whose effect is based on generally improving cerebral blood flow.

The problem of the invention is to find a use for an agent which reduces the symptoms of Parkinson's disease when taken alone, but in particular in combination with known agents.

For a use of the abovementioned kind this problem is solved by adding a local anesthetic of the anilide group or its derivatives as an effective substance for preparing a medication for treating the symptoms of Parkinson's disease.

Preferred embodiments of the invention are the subject matter of the subclaims.

According to a preferred embodiment of the inventive use, the local anesthetic of the anilide group chosen is the substance mepivacaine, preferably in a daily dose of 30 mg to 60 mg. Alternatively to mepivacaine one can use the substances lidocaine, bupivacaine, butanilicaine, tolycaine or etidocaine.

The inventive use has the effect, upon application to parkinsonian patients, that the specific symptoms of Parkinson's disease clearly subside, the resulting improved condition of the patient continuing for several hours and even days. In particular, a clear improvement of disease-specific symptoms was obtained with the inventive use insofar as

- motoricity and fine motoricity were improved
- mobility was increased
- concentration power was increased
- reaction time was decreased
- pronunciation was improved
- power of comprehension was improved
- state of mind was brightened and emotional condition improved.

With the inventive use, the combination of a substance increasing dopamine concentration in the synaptic cleft of the neurons of the brain with a local anesthetic of the anilide group possibly results in an increase in the permeability of the blood-brain barrier for the substance levodopa, so that dopamine can accumulate in higher concentration in the brain of a person suffering from Parkinson's disease than with standard treatment, thereby obtaining a higher concentration of dopamine in such a person's brain. In addition, it possibly increases the retention time of dopamine in the brain.

The substance "local anesthetic of the anilide group" essential to the inventive use belongs in general to the local anesthetics of different structure, the local anesthetics of the anilide group and their derivatives being preferred for treatment as a subgroup of said local anesthetics. Examples of said subgroup are not only mepivacaine but also lidocaine, bupivacaine, butanilicaine, etidocaine and tolycaine. Mepivacaine has the smallest molecule of said group, and said substance has also proved most effective in treating patients with Parkinson's disease. One supposition is that the small molecular size of mepivacaine provides an increased probability of crossing the blood-brain barrier. Mepivacaine is in addition lipophilic, i.e. lipid-loving, and tends to attach to fat molecules. It is remarkable in this connection that neurons are usually embedded in fat and an accumulation or concentration of mepivacaine in fat will presumably also have effects on the nervous pathways running through fatty tissue. Levodopa also has strong lipophilia, like mepivacaine, so that this connection might also provide a mechanism of action.

In the inventive use for treating the symptoms of Parkinson's disease, levodopa is preferably applied in a daily dose of 200 mg to 600 mg.

According to an alternative embodiment of the inventive use, the substance increasing dopamine concentration in the synaptic cleft of the neurons of the brain additionally contains bromocriptine, which is preferably applied in a daily dose of 1.25 mg to 10 mg.

According to another embodiment of the inventive use, the substance increasing dopamine concentration in the synaptic cleft of the neurons of the brain additionally contains selegiline, which is preferably applied in a daily dose of 4 mg to 20 mg.

According to another alternative embodiment of the inventive use, the substance increasing dopamine concentration in the synaptic cleft of the neurons of the brain additionally contains amantadine, which is preferably applied in a daily dose of 100 mg to 400 mg.

According to another alternative embodiment of the inventive use, the substance increasing dopamine concentration in the synaptic cleft of the neurons of the brain additionally contains pergolide mesylate, which is preferably applied in a daily dose of 2 mg to 8 mg. The inventive agent, according to another embodiment, can also contain tolcapone as a substance increasing dopamine concentration in the synaptic cleft of the neurons of the brain, which is applied in a daily dose of 100 mg to 400 mg.

According to another inventive embodiment of the inventive use, the substance increasing dopamine concentration in the synaptic cleft of the neurons of the brain could additionally contain piracetam, which is applied in a daily dose of 1,000 mg to 4,000 mg.

The abovementioned substances increasing dopamine concentration in the synaptic cleft of the neurons of the brain can according to the invention be contained in the inventive use of an agent both each per se and in different combinations with each other. However, the effect of the agent is based not so much on a special combination of substances increasing dopamine concentration in the synaptic cleft of the neurons of the brain as used in classical parkinsonian treatment, but rather on a combination of said substances classically used for parkinsonian treatment with a local anesthetic, in particular a local anesthetic of the anilide group and more particularly, but not exclusively, with the substance mepivacaine.

The stated doses of local anesthetics are based on applications by injection. For oral application the dose is to be adapted accordingly.

What is claimed is:

1. A method for treating the symptoms of Parkinson's disease comprising:
   administering to a person in need of treating, a therapeutically effective amount of a substance which increases Dopamine concentration in the synaptic cleft of the neurons of the brain, in combination with an effective amount of a local anesthetic of the anilide group or derivatives thereof,
   wherein the local anesthetic of the anilide group is selected from the group consisting of mepivacaine, bupivacaine, butanilicaine, tolycaine, etidocaine, and mixtures thereof.
2. The method according to claim 1, wherein
   the local anesthetic of the anilide group is mepivacaine.
3. The method according to claim 2, wherein mepivacaine is applied in a daily dose of 30 mg to 60 mg.
4. The method according to claim 1, wherein
   the local anesthetic of the anilide group is bupivacaine.
5. The method according to claim 4, wherein bupivacaine is applied in a daily dose of up to 150 mg.
6. The method according to claim 1, wherein
   the local anesthetic of the anilide group is butanilicaine.
7. The method according to claim 1, wherein
   the local anesthetic of the anilide group is tolycaine.
8. The method according to claim 1, wherein
   the local anesthetic of the anilide group is etidocaine.
9. The method according to claim 1, wherein the substance which increases dopamine concentration in the synaptic cleft of the neurons of the brains is LevoDopa and is applied in a daily dose of 200 mg to 600 mg.
10. The method according to claim 1, wherein
    the substance increasing dopamine concentration in the synaptic cleft of the neurons of the brain additionally contains bromocriptine.
11. The method according to claim 10, wherein bromocriptine is applied in a daily dose of 1.0 mg to 10 mg.
12. The method according to claim 1, wherein
    the substance increasing dopamine concentration in the synaptic cleft of the neurons of the brain additionally contains selegiline.
13. The method according to claim 12, wherein
    selegiline is applied in a daily dose of 4 mg to 20 mg.
14. The method according to claim 1, wherein
    the substance increasing dopamine concentration in the synaptic cleft of the neurons of the brain additionally contains amantadine.
15. The method according to claim 14, wherein
    amantadine is applied in a daily dose of 100 mg to 400 mg.
16. The method according to claim 1, wherein
    the substance increasing dopamine concentration in the synaptic cleft of the neurons of the brain additionally contains pergolide mesylate.
17. The method according to claim 16, wherein
    pergolide mesylate is applied in a daily dose of 2 mg to 8 mg.
18. The method according to claim 1, wherein
    the substance increasing dopamine concentration in the synaptic cleft of the neurons of the brain additionally contains tolcapone.
19. The method according to claim 18, wherein
    tolcapone is applied in a daily dose of 100 mg to 400 mg.
20. The method according to claim 1,
    wherein the substance increasing dopamine concentration in the synaptic cleft of the neurons of the brain additionally contains piracetam.
21. The method according to claim 20, wherein
    piracetam is applied in a daily dose of 1000 mg to 4000 mg.

* * * * *